US007005031B2

(12) United States Patent
Lucast et al.

(10) Patent No.: US 7,005,031 B2
(45) Date of Patent: Feb. 28, 2006

(54) PRESSURE SENSITIVE ADHESIVES HAVING QUATERNARY AMMONIUM FUNCTIONALITY, ARTICLES, AND METHODS

(75) Inventors: Donald H. Lucast, North St. Paul, MN (US); Dong-Wei Zhu, Woodbury, MN (US)

(73) Assignee: 3M Innovative Properties Company, St. Paul, MN (US)

(*) Notice: Subject to any disclaimer, the term of this patent is extended or adjusted under 35 U.S.C. 154(b) by 338 days.

(21) Appl. No.: 10/052,032

(22) Filed: Jan. 16, 2002

(65) Prior Publication Data

US 2003/0175503 A1  Sep. 18, 2003

(51) Int. Cl.
C08L 15/00 (2006.01)
(52) U.S. Cl. ............... 156/330.9; 523/111; 528/71; 424/78.06; 424/78.07; 424/78.35; 424/78.37; 156/332
(58) Field of Classification Search .......... 156/330.9, 156/331.1, 333, 327; 523/111; 528/71; 424/78.06, 78.07, 78.08, 78.35, 78.37
See application file for complete search history.

(56) References Cited

U.S. PATENT DOCUMENTS

| 3,216,983 | A |   | 11/1965 | Shelanski et al. |
| 3,305,510 | A |   | 2/1967 | Gander ............... 260/33.2 |
| 3,380,923 | A |   | 4/1968 | Beach |
| 4,199,564 | A |   | 4/1980 | Silver et al. |
| 4,356,229 | A | * | 10/1982 | Brodnyan et al. ......... 442/86 |
| 4,542,012 | A |   | 9/1985 | Dell |
| 4,584,192 | A |   | 4/1986 | Dell et al. |
| 4,598,004 | A |   | 7/1986 | Heinecke |
| 4,728,323 | A |   | 3/1988 | Matson |
| 4,952,618 | A |   | 8/1990 | Olsen |
| 4,978,527 | A |   | 12/1990 | Brink et al. |
| 5,173,291 | A |   | 12/1992 | Brink et al. |
| 5,408,022 | A |   | 4/1995 | Imazato et al. |
| 5,437,932 | A |   | 8/1995 | Ali et al. |
| 5,494,987 | A |   | 2/1996 | Imazato et al. |
| 5,529,770 | A |   | 6/1996 | McKinzie et al. |
| 5,614,310 | A |   | 3/1997 | Delgado et al. |
| 5,618,841 | A |   | 4/1997 | Kross |
| 5,621,058 | A |   | 4/1997 | Kondo et al. |
| 5,733,949 | A |   | 3/1998 | Imazato et al. |
| 5,800,685 | A |   | 9/1998 | Perrault |
| 5,817,344 | A |   | 10/1998 | Hoang et al. |
| 5,874,074 | A |   | 2/1999 | Smith ............... 424/78.02 |
| 5,908,693 | A | * | 6/1999 | Delgado et al. ......... 428/343 |
| 6,034,129 | A |   | 3/2000 | Mandeville, III et al. |
| 6,039,940 | A | * | 3/2000 | Perrault et al. ......... 424/78.06 |
| 6,133,391 | A |   | 10/2000 | Nielson et al. |
| 6,194,530 | B1 |  | 2/2001 | Klesse et al. |
| 6,198,016 | B1 |  | 3/2001 | Lucast et al. |

| 2003/0032352 | A1 | * | 2/2003 | Chang et al. ............... 442/102 |

FOREIGN PATENT DOCUMENTS

| DE | 40 24 192 A1 | 2/1992 |
| JP | 5-295317 A | 11/1993 |
| JP | 8-89779 A | 4/1996 |
| JP | 8-325538 A | 12/1996 |
| JP | 11-228609 A | 8/1999 |
| JP | 11-269448 A | 10/1999 |
| JP | 2-983449 B2 | 11/1999 |
| WO | WO 86/05391 | 9/1986 |
| WO | WO 93/07903 | 4/1993 |
| WO | WO 96/20227 | 7/1996 |
| WO | WO 99/22934 | 5/1999 |
| WO | WO 00/15356 | 3/2000 |
| WO | WO 01/16193 A1 | 7/2000 |
| WO | WO 00/69926 | 11/2000 |
| WO | WO 01/85867 A1 | 11/2001 |
| WO | WO 02/058757 A1 | 8/2002 |
| WO | WO 02/060417 A1 | 8/2002 |

OTHER PUBLICATIONS

ASTM E 96-80, "Standard Test Methods for Water Vapor Transmission of Materials," *Annual Book of ASTM Standards*, Part 20, Title page and pp. 742-751 (1981).
Fred Billmeyer, Jr. (Ed.) *Textbook of Polymer Science*, 2nd Edition, Wiley-Interscience, NY, Title page, Publicaiton page, Table of Contents and pp. 84-85 (1971).
"PSTC-1, Peel Adhesion of Single Coated Pressure Sensitive Tapes at 180° Angle," *Test Methods For Pressure Sensitive Adhesive Tapes*, 12th Edition, Pressure Sensitive Tape Council, Chicago, III., Title page, table of contents, and pp. 23-24 (1996).
Donatas Satas (Ed.), *Handbook of Pressure Sensitive Adhesive Technology*, 2nd Edition, Van Nostrand Reinhold, New York, NY, Title page, Publication page and p. 172 (1989).
Donatas Satas (Ed.). Handbbook of Pressure Sensitive Adhesive Technology, 2nd Edition, Van Nostrand Reinhold, New York, NY. Title page and pp. 168 and 269 (1989).

* cited by examiner

*Primary Examiner*—Sam Chuan Yao
(74) *Attorney, Agent, or Firm*—Nancy M. Lambert

(57) ABSTRACT

A pressure sensitive adhesive composition is provided that includes a pressure sensitive adhesive polymer. The polymer includes: at least one copolymerized monoethylenically unsaturated (meth)acrylic acid ester monomer, wherein the (meth)acrylic acid ester monomer, when homopolymerized, has a Tg of less than about 25° C.; at least one copolymerized monoethylenically unsaturated reinforcing monomer, wherein the reinforcing monomer, when homopolymerized, has a Tg of at least about 25° C.; covalently bonded quarternary ammonium functionality; and, optionally, at least one copolymerized monoethylenically unsaturated poly(alkylene oxide) monomer. The composition optionally further includes at least one nonreactive poly(alkylene oxide) polymer and/or at least one antimicrobial agent.

40 Claims, No Drawings

PRESSURE SENSITIVE ADHESIVES HAVING QUATERNARY AMMONIUM FUNCTIONALITY, ARTICLES, AND METHODS

FIELD OF THE INVENTION

This invention pertains to a pressure sensitive adhesive and more particularly to a pressure sensitive adhesive containing quaternary ammonium functionality, which preferably can provide antimicrobial activity.

BACKGROUND

Pressure sensitive adhesive (PSA) articles are used in a wide variety of applications where there is a need to adhere to skin, for example, medical tapes, wound or surgical dressings, athletic tapes, surgical drapes, or tapes or tabs used in adhering medical devices such as sensors, electrodes, ostomy appliances, or the like. A concern with many of these adhesive articles is the need to balance the objectives of providing sufficiently high levels of adhesion while providing antimicrobial activity.

Approaches in the art to providing pressure sensitive adhesive articles with antimicrobial activity include depositing an antimicrobially effective layer of a silver salt on the adhesive surface of a wound dressing or incorporating an antimicrobial agent, e.g., iodine or chlorhexidine salts, into pressure sensitive adhesive microspheres prior to coating on a suitable wound dressing backing.

(Meth)acrylate pressure sensitive adhesives are attractive materials for many applications. (Meth)acrylates are known for their optical clarity, oxidative resistance, and inherently tacky nature. Inherently tacky (meth)acrylate pressure sensitive adhesives (i.e., materials that require no additives such as tackifying resins) are typically formulated predominately from acrylic acid ester monomers. Examples of such monomers include n-butyl acrylate, 2-ethylhexyl acrylate, isooctyl acrylate, isononyl acrylate, isodecyl acrylate, and dodecyl acrylate. When these (meth)acrylate monomers are polymerized, the homopolymers have a glass transition temperature (Tg) of less than about 25° C. This low Tg is a necessary property in (meth)acrylate materials that exhibit tack at room temperature.

A means of reinforcing (meth)acrylate polymers is to copolymerize the (meth)acrylate monomers with acidic comonomers, such as acrylic acid, methacrylic acid, beta-carboxyethyl acrylate, itaconic acid, sulfoethyl acrylate, and the like. Addition of these acidic comonomers in minor amounts (e.g., about 1 weight percent to about 15 weight percent) can enhance the internal or cohesive strength of the PSA. This increased polymer reinforcement, however, can diminish the tack of the acidic comonomer-containing (meth)acrylate copolymer, which is often undesirable. Furthermore, there is a desire to eliminate such acidic components in pressure sensitive adhesives, particularly for use on skin. Such components can deactivate antimicrobial agents, for example.

Thus, there is a continuing need for pressure sensitive adhesives, particularly (meth)acrylate adhesives that can be used in medical applications, for example, that are either inherently antimicrobial and/or are compatible with added antimicrobial agents.

SUMMARY OF INVENTION

The present invention provides a pressure sensitive adhesive composition that includes a pressure sensitive adhesive polymer, optionally a nonreactive poly(alkylene oxide) polymer, and optionally an antimicrobial agent. Preferred embodiments of the pressure sensitive adhesive composition include a chlorhexidine-compatible pressure sensitive adhesive polymer. As used herein, a chlorhexidine-compatible pressure sensitive adhesive is one that is compatible with chlorhexidine and aqueous solutions of chlorhexidine. Also, preferred embodiments of the pressure sensitive adhesive composition of the present invention adhere to wet skin.

Although the pressure sensitive adhesives described herein include quaternary ammonium functionality, other amine groups can be included in addition to or in place of the quaternary ammonium groups. These include, for example, amine oxide groups and protonated tertiary amine groups.

In one embodiment, the pressure sensitive adhesive polymer includes: at least one copolymerized monoethylenically unsaturated (meth)acrylic acid ester monomer, wherein the (meth)acrylic acid ester monomer, when homopolymerized, has a Tg of less than about 25° C.; and at least one copolymerized monoethylenically unsaturated reinforcing monomer, wherein the reinforcing monomer, when homopolymerized, has a Tg of at least about 25° C.; wherein the pressure sensitive adhesive polymer includes covalently bonded quaternary ammonium functionality. Preferably, the copolymerized monoethylenically unsaturated reinforcing monomer is a quaternary ammonium monomer.

In another embodiment, the pressure sensitive adhesive polymer includes: at least one copolymerized monoethylenically unsaturated (meth)acrylic acid ester monomer, wherein the (meth)acrylic acid ester monomer, when homopolymerized, has a Tg of less than about 25° C.; and at least one copolymerized quaternary ammonium monomer, wherein the quaternary ammonium monomer, when homopolymerized, has a Tg of at least about 25° C.

Optionally, a pressure sensitive adhesive polymer of the present invention further includes at least one copolymerized monoethylenically unsaturated poly(alkylene oxide) monomer. Preferably, this monomer is a poly(alkylene oxide) (meth)acrylic acid ester monomer.

Preferably, the pressure sensitive adhesive polymer has a Tg of no greater than about 10° C., more preferably, no greater than about −10° C., and most preferably, no greater than about −20° C.

The nonreactive poly(alkylene oxide) polymer preferably includes copolymerized monomers selected from the group consisting of ethylene oxide, propylene oxide, butylene oxide, trimethylene oxide, tetramethylene oxide, their corresponding glycols, and mixtures thereof.

A pressure sensitive adhesive composition of the present invention can be inherently antimicrobial. Alternatively, a pressure sensitive adhesive composition of the present invention can include at least one antimicrobial agent. If used, an antimicrobial agent is preferably present in an amount of at least about 0.05 wt-%, based on the total weight of the pressure sensitive adhesive composition. The antimicrobial agent is preferably selected from the group consisting of iodine, complexed forms of iodine, chlorhexidine salts, parachlorometaxylenol, triclosan, hexachlorophene, fatty acid esters, phenols, surfactants having a C12–C22 hydrophobe and a quaternary ammonium group, quaternary amines, quaternary silanes, hydrogen peroxide, silver, silver salts, silver oxide, silver sulfadiazine, and combinations thereof. More preferably, the antimicrobial agent is a chlorhexidine salt.

A preferred embodiment of the present invention provides a pressure sensitive adhesive composition that includes at least one antimicrobial agent and a pressure sensitive adhesive polymer including: at least one copolymerized monoethylenically unsaturated (meth)acrylic acid ester monomer, wherein the (meth)acrylic acid ester monomer, when homopolymerized, has a Tg of less than about 25° C.; at least one copolymerized quaternary ammonium monomer, wherein the quaternary ammonium monomer, when homopolymerized, has a Tg of at least about 25° C.; and at least one copolymerized poly(alkylene oxide) (meth)acrylic acid ester monomer.

Another preferred embodiment of the present invention provides a pressure sensitive adhesive composition that includes: at least one nonreactive poly(alkylene oxide) polymer; and a pressure sensitive adhesive polymer including: at least one copolymerized monoethylenically unsaturated (meth)acrylic acid ester monomer, wherein the (meth) acrylic acid ester monomer, when homopolymerized, has a Tg of less than about 25° C.; and at least one copolymerized quaternary ammonium monomer, wherein the quaternary ammonium monomer, when homopolymerized, has a Tg of at least about 25° C.

Another preferred embodiment of the present invention provides a pressure sensitive adhesive composition that includes: at least one antimicrobial agent; at least one nonreactive poly(alkylene oxide) polymer; and a pressure sensitive adhesive polymer including: at least one copolymerized monoethylenically unsaturated (meth)acrylic acid ester monomer, wherein the (meth)acrylic acid ester monomer, when homopolymerized, has a Tg of less than about 25° C.; and at least one copolymerized quaternary ammonium monomer, wherein the quaternary ammonium monomer, when homopolymerized, has a Tg of at least about 25° C.

In yet another embodiment of the present invention, a pressure sensitive adhesive polymer includes: at least one copolymerized monoethylenically unsaturated (meth)acrylic acid ester monomer, wherein the (meth)acrylic acid ester monomer, when homopolymerized, has a Tg of less than about 25° C.; and at least one copolymerized monoethylenically unsaturated reinforcing monomer, wherein the reinforcing monomer, when homopolymerized, has a Tg of at least about 25° C.; wherein the pressure sensitive adhesive polymer includes covalently bonded quaternary ammonium functionality and no more than about 5 weight percent of copolymerized acidic monomers, based on the total weight of pressure sensitive adhesive polymer.

The present invention also provides an article that includes a backing and a pressure sensitive adhesive composition as described herein on at least a portion of a surface thereof. Preferably, the article is a medical article, which preferably adheres to wet skin. More preferably, the article has an initial wet skin adhesion of at least about 0.8 N/dm, and most preferably, at least about 1.6 N/dm. Preferably, the article adheres to dry skin with an initial dry skin adhesion of at least about 0.8 N/dm. Preferably, the initial wet skin adhesion that is at least about 65% of the initial dry skin adhesion.

The present invention also provides a method of making a pressure sensitive adhesive composition. The method includes combining under conditions effective to cause polymerization components including: at least one monoethylenically unsaturated (meth)acrylic acid ester monomer, which when homopolymerized, has a Tg of less than about 25° C.; at least one quaternary ammonium monomer, wherein the quaternary ammonium monomer, when homopolymerized, has a Tg of at least about 25° C.; and optionally at least one monethylenically unsaturated poly (alkylene oxide) monomer. The method preferably involves copolymerizing the monomers prior to the addition of at least one nonreactive poly(alkylene oxide) polymer and/or prior to the addition of at least one antimicrobial agent.

The present invention further provides a method of using an adhesive article. The method includes: providing an adhesive article as described herein and adhering the adhesive article to skin.

As used herein:

"pressure sensitive adhesive" or "PSA" refers to a viscoelastic material that displays tackiness and adheres well to a wide variety of substrates after applying only light pressure (e.g., finger pressure). One well known means of identifying pressure sensitive adhesives is the Dahlquist criterion. This criterion defines a pressure sensitive adhesive as an adhesive having a 1 second creep compliance of greater than $1 \times 10^{-6}$ cm$^2$/dyne as described in *Handbook of Pressure Sensitive Adhesive Technology*, Donatas Satas (Ed.), 2$^{nd}$ Edition, p. 172, Van Nostrand Reinhold, New York, N.Y., 1989;

"(meth)acrylate monomers" are acrylic acid esters or methacrylic acid esters of alcohols, preferably having about 4 to 14 carbon atoms;

"quaternary ammonium monomers" are copolymerizable monoethylenically unsaturated organo-ammonium salts;

"poly(alkylene oxide) monomers" are monoethylenically unsaturated poly(alkylene oxides);

"nonreactive poly(alkylene oxide) polymers" are polymers that do not contain free radically reactive ethylenically unsaturated groups that could react with the (meth)acrylate monomers, quaternary ammonium monomers, or poly(alkylene oxide) monomers and do not significantly inhibit the polymerization of these monomers;

"polymer" includes homopolymers and copolymers;

"copolymer" includes a polymer of any length (including oligomers) of two or more types of polymerizable monomers, and therefore includes terpolymers, tetrapolymers, etc., which can include random copolymers, block copolymers, or sequential copolymers; and "nonreactive" refers to components that do not contain free radically reactive ethylenically unsaturated groups that could react with other components (e.g., monomers) or functional groups thereon and significantly inhibit the polymerization or adversely affect the function of the pressure sensitive adhesive.

DETAILED DESCRIPTION OF PREFERRED EMBODIMENT(S)

Generally, the pressure sensitive adhesive composition of the present invention includes a pressure sensitive adhesive polymer that includes covalently bonded quaternary ammonium functionality, at least one copolymerized monoethylenically unsaturated (meth)acrylic acid ester monomer, and at least one copolymerized reinforcing monomer (preferably, a quaternary ammonium monomer). The (meth)acrylic acid ester monomer, when homopolymerized, has a Tg of less than about 25° C., and the reinforcing monomer (preferably, the quaternary ammonium monomer), when homopolymerized, has a Tg of at least about 25° C.

In certain embodiments, the pressure sensitive adhesive polymer also includes a copolymerized monoethylenically unsaturated poly(alkylene oxide) monomer. Alternatively, or additionally, the pressure sensitive adhesive polymer can be combined with a nonreactive poly(alkylene oxide) polymer.

Preferably, the pressure sensitive adhesive polymer itself is antimicrobial (i.e., it is inherently antimicrobial). Alternatively, and more preferably, one or more additional antimicrobial agents are combined with the pressure sensitive adhesive polymer to enhance its antimicrobial activity.

The ratio of each monomer in the pressure sensitive adhesive polymer can be chosen to optimize the performance characteristics of the adhesive. For example, higher levels of the reinforcing monomer (preferably, the quaternary ammonium monomer) can increase the overall Tg and the stiffness of the pressure sensitive adhesive. However, the increased Tg (and modulus) may necessitate higher levels of the optional copolymerized monoethylenically unsaturated poly(alkylene oxide) monomer and/or the optional nonreactive poly(alkylene oxide) polymer. Depending on the desired end use, higher or lower levels of the optional copolymerized monoethylenically unsaturated poly(alkylene oxide) monomer and/or the optional nonreactive poly(alkylene oxide) polymer may be beneficial. For example, if high cohesive strength is desired, typically lower levels of poly(alkylene oxide) monomer and/or poly(alkylene oxide) polymer are used.

Preferably, the pressure sensitive adhesive polymer has a Tg of no greater than about 10° C., and more preferably, no greater than about −10° C., and most preferably, no greater than about −20° C. One method of measuring the Tg of a polymer may involve the utilization of a Differential Scanning Calorimeter (DSC, e.g., the PYRIS 7-Series Thermal Analyzer, Perkin-Elmer, Shelton, CN) in the range of −100° C. to +100° C. at a rate of 20° C. per minute.

Preferably, the pressure sensitive adhesive polymer includes little or no copolymerized acidic monomers such as ethylenically unsaturated carboxylic acids, ethylenically unsaturated sulfonic acids, ethylenically unsaturated phosphonic acids, and mixtures thereof. More preferably, the pressure sensitive adhesive polymer includes no more than about 5 weight percent, even more preferably, no more than about 1 weight percent, and most preferably, no more than about 0.1 weight percent, of copolymerized acidic monomers, based on the total weight of pressure sensitive adhesive polymer. Examples of such compounds include, but are not limited to, acrylic acid, methacrylic acid, itaconic acid, fumaric acid, crotonic acid, citraconic acid, maleic acid, β-carboxyethyl acrylate, 2-sulfoethyl methacrylate, styrene sulfonic acid, 2-acrylamido-2-methylpropane sulfonic acid, vinyl phosphonic acid, and the like.

The present invention also provides articles that include a backing (i.e., substrate) having a continuous or discontinuous adhesive layer disposed thereon (i.e., at least a portion of a surface thereof has a pressure sensitive adhesive composition of the present invention disposed thereon). Preferably, such articles have a peel adhesion value to glass of at least about 16 Newtons per decimeter (N/dm) and a shear value to stainless steel of at least about 60 minutes, using the procedures described in the Examples Section.

Preferably, such articles have an initial wet skin adhesion of at least about 20 grams (g) per 2.5 centimeters (cm) (0.8 N/dm), and more preferably, at least about 40 g/2.5 cm (1.6 N/dm). Preferably, the initial dry skin adhesion is at least about 20 g/2.5 cm (0.8 N/dm), and more preferably, at least about 40 g/2.5 cm (1.6 N/dm). Preferably, the adhesive article (i.e., a substrate with a continuous or discontinuous layer of adhesive disposed thereon) has an initial wet skin adhesion that is at least about 65%, more preferably, at least about 75%, and most preferably, at least about 100%, of the initial dry skin adhesion. The comparison of wet to dry skin adhesion can be carried out using the test protocol described in the Examples Section. Herein, wet skin has visually observable water thereon.

(Meth)acrylate Monomers

The pressure sensitive adhesive polymers of the present invention contain at least one copolymerized monoethylenically unsaturated (meth)acrylic acid ester (i.e., an alkyl acrylate or alkyl methacrylate), wherein the alkyl group typically has at least about 4 carbon atoms (on average). Alternatively stated, these (meth)acrylate monomers are (meth)acrylic acid esters of alkyl alcohols (preferably, nontertiary alkyl alcohols), the alkyl groups of which preferably include about 4 to about 14, more preferably about 4 to about 8, carbon atoms (on average). The alkyl group can optionally contain heteroatoms and can be linear or branched. When homopolymerized, these monomers yield inherently tacky polymers with glass transition temperatures that are typically below about 25° C. Preferred (meth)acrylate monomers have the following general Formula (I):

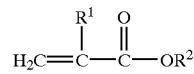

Formula (I)

wherein $R^1$ is H or $CH_3$, the latter corresponding to where the (meth)acrylate monomer is a methacrylate monomer, and $R^2$ is broadly selected from linear or branched organic groups and optionally includes one or more heteroatoms. The number of carbon atoms in the organic group is preferably about 4 to about 14, and more preferably about 4 to about 8.

Examples of suitable (meth)acrylate monomers useful in the present invention include, but are not limited to, n-butyl acrylate, decyl acrylate, 2-ethylhexyl acrylate, hexyl acrylate, isoamyl acrylate, isodecyl acrylate, isononyl acrylate, isooctyl acrylate, lauryl acrylate, 2-methylbutyl acrylate, 4-methyl-2-pentyl acrylate, ethoxy ethoxyethyl acrylate, and the like. Various combinations of these monomers can be used if desired. Particularly preferred are n-butyl acrylate, 2-ethylhexyl acrylate, isooctyl acrylate, lauryl acrylate, and mixtures thereof. Various combinations of monoethylenically unsaturated (meth)acrylate monomers can be used in the pressure sensitive adhesives of the present invention.

Preferably, a copolymerizable mixture of monomers of the present invention includes, based upon the total weight of the copolymerizable monomers, at least about 40 weight percent (wt-%), more preferably, at least about 50 wt-%, and most preferably, at least about 60 wt-%, of the (meth)acrylate monomer(s). Preferably, a copolymerizable mixture of monomers of the present invention includes, based upon the total weight of the copolymerizable monomers, no greater than about 95 wt-%, more preferably, no greater than about 90 wt-%, and most preferably, no greater than about 85 wt-%, of the (meth)acrylate monomer(s).

Reinforcing Monomers

The pressure sensitive adhesive polymers of the present invention contain at least one copolymerized monoethylenically unsaturated reinforcing monomer that, when homopolymerized, has a Tg of at least about 25° C. The reinforcing monomer can be (meth)acrylic acids, (meth)acrylates, (meth)acrylamides, and the like.

Preferably, the reinforcing monomer is a quaternary ammonium monomer, which is a salt having an organo-ammonium group and a monoethylenically unsaturated group. Preferably, the quaternary ammonium monomer has the following general Formula (II):

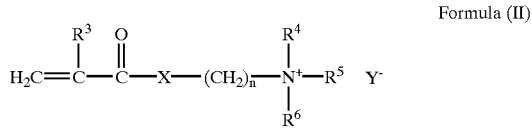

Formula (II)

wherein: n is about 2 to about 10, preferably about 2 to about 3; $R^3$ is H or $CH_3$; $R^4$, $R^5$, and $R^6$ are each independently linear or branched organic groups, preferably having about 1 to about 16 carbon atoms (on average); X is O or NH; and $Y^-$ is an acceptable anionic counterion to the $N^+$ of the quaternary ammonium group (e.g., one that does not adversely affect the polymerization of the monomers or antimicrobial activity of an added antimicrobial agent).

Preferably, $R^4$, $R^5$, and $R^6$ are each independently alkyl, aryl, alkaryl, or aralkyl groups. Alkyl groups are preferably lower alkyl, having about 1 to about 16 carbon atoms (on average) with methyl and ethyl groups being particularly preferred. Aryl is preferably phenyl but can be any suitable aromatic moiety such as those selected from the group consisting of phenyl, thiophenyl, naphthyl, biphenyl, pyridyl, pyrimidinyl, pyrazyl, pyridazinyl, furyl, thienyl, pyrryl, quinolinyl, bipyridyl, and the like. Representative of an aralkyl grouping is benzyl and representative of an alkaryl grouping is tolyl. X is preferably O. Representative counterions ($Y^-$) are $Cl^-$, $Br^-$, $HSO_4^-$, $CH_3CH_2OSO_3^-$, and $CH_3OSO_3^-$, with the sulfate salts being particularly preferred. In certain embodiments, the chloride counterion may interfere with the antimicrobial activity of an added antimicrobial agent. Alkyl groups can be straight or branched chain and alkyl and aryl groups can be substituted by non-interfering substituents that do not obstruct with the functionality of the polymers.

Useful copolymerizable quaternary ammonium monomers include, but are not limited to, those selected from 2-(meth)acryloxyethyl trialkyl ammonium halides and sulfates, and mixtures thereof. Examples of such compounds include, but are not limited to, 2-(meth)acryloxyethyl trimethyl ammonium chloride, $CH_2=C(H$ or $CH_3)$ $CO_2CH_2CH_2N(CH_3)_3Cl$; 2-(meth)acryloxyethyl trimethyl ammonium methyl sulfate, $CH_2=C(H$ or $CH_3)$ $CO_2CH_2CH_2N(CH_3)_3OSO_2OCH_3$; 2-(meth)acryloxyethyl methyl diethyl ammonium methyl sulfate, $CH_2=C(H$ or $CH_3)CO_2CH_2CH_2N(CH_3)(C_2H_5)_2OSO_2OCH_3$; 2-(meth) acryloxyethyl dimethyl benzyl ammonium chloride, $CH_2=C(H$ or $CH_3)CO_2CH_2CH_2N(CH_3)_2(C_6H_5CH_2)Cl$ (all of the preceding monomers available from Ciba Specialty Chemicals, Woodbridge, N.J.); 2-(methylacryloxy)ethyl dimethyl hexadecyl ammonium bromide, $CH_2=C(CH_3)$ $CO_2CH_2CH_2N(CH_3)_2(C_{16}H_{33})Br$ (described in Example 1 of U.S. Pat. No. 5,437,932 (Ali et al.)); and the like. Various combinations of these monomers can be used if desired. Due to their availability, effectiveness in reinforcing (meth)acrylate pressure sensitive adhesives, and their antimicrobial activity, particularly preferred quaternary ammonium monomers are 2-acryloxyethyl trimethyl ammonium methyl sulfate and 2-acryloxyethyl methyl diethyl ammonium methyl sulfate. Such monomers are typically hydrophilic. Various combinations of monoethylenically unsaturated reinforcing monomers can be used in the pressure sensitive adhesive polymers of the present invention.

Preferably, a copolymerizable mixture of monomers of the present invention includes, based upon the total weight of the copolymerizable monomers, at least about 5 wt-%, more preferably, at least about 10 wt-%, and most preferably, at least about 15 wt-%, by weight of the reinforcing monomer(s) (preferably, quaternary ammonium monomer(s)). Preferably, a copolymerizable mixture of monomers of the present invention includes, based upon the total weight of the copolymerizable monomers, no greater than about 60 wt-%, more preferably, no greater than about 50 wt-%, and most preferably, no greater than about 40 wt-%, of the reinforcing monomer(s) (preferably, quaternary ammonium monomer(s)).

As an alternative approach to providing the pressure sensitive adhesive copolymers of the present invention that contain a quaternary ammonium functional unit, it is possible to start with an amine monomer and form the quaternary ammonium unit following polymerization. Preferably, the amine monomers have the following general Formula (III):

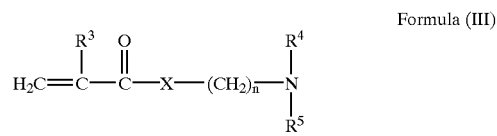

Formula (III)

wherein n, $R^3$, $R^4$, $R^5$, and X are the same as defined for Formula (II).

Following polymerization of one or more such amine monomers with one or more monomers of Formula (I) and optionally one or more optional poly(alkylene oxide) monomers (described below), the resulting copolymer is reacted with an organic compound of structure $R^6Z$ to incorporate covalently bonded quaternary ammonium functionality, wherein $R^6$ is the same as defined for Formula (II) and Z is a functional group capable of forming the counterion Y as defined for Formula (II).

Although the pressure sensitive adhesives described herein include quaternary ammonium functionality, other amine groups can be included in addition to or in place of the quaternary ammonium groups. These include, for example, amine oxide groups and protonated tertiary amine groups. Such polymers can be prepared from monoethylenically unsaturated amine group-containing monomers, such as monoethylenically unsaturated quaternary amine, amine oxide, and/or protonated tertiary amine group-containing monomers. Most preferred side chain amine group-containing monomers are monoethylenically unsaturated quaternary amine, amine oxide, tertiary amine, or protonated tertiary amine group-containing (meth)acrylic monomers. The most preferred monoethenically unsaturated amine group-containing monomers from which to form the pressure sensitive adhesives are quaternary amine and tertiary amine group-containing monomers. If desired, the tertiary amine groups can be easily converted to protonated tertiary amine groups, amine oxide groups, or quaternary ammonium groups by the appropriate chemical reaction as described in Applicants' Assignee's copending U.S. patent application Ser. No. 10/052,158, filed on even date herewith, entitled FILM-FORMING COMPOSITIONS AND METHODS.

Optional Poly(Alkylene Oxide) Monomers

One or more monoethylenically unsaturated poly(alkylene oxide) monomers can be copolymerized with the (meth)

acrylate and reinforcing (preferably, quaternary ammonium) monomers. The monoethylenically unsaturated poly(alkylene oxide) monomers are selected for use in the pressure sensitive adhesive such that they optimize the pressure sensitive adhesive properties (e.g., increase tack) of the copolymerized (meth)acrylate and reinforcing monomers for a particular purpose.

The monoethylenically unsaturated poly(alkylene oxide) monomers preferably have the following general Formula (IV):

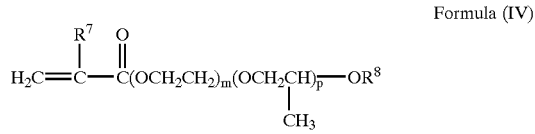

Formula (IV)

wherein: m is about 1 to about 50; p is 0 to about 50; $R^7$ is H or $CH_3$, and $R^8$ is hydrogen or linear or branched organic groups, preferably having about 1 to about 4 carbon atoms (on average). In this representation, the isopropylene oxide groups (the "p" groups) and the ethylene oxide groups (the "m" groups) can be arranged in a reversed, alternating, random, or block configuration. In any one monomer, m is preferably at least about 4 and no greater than about 25. Preferably, p is 0. Preferably, $R^8$ is methyl.

Preferably, the monoethylenically unsaturated poly(alkylene oxide) monomers are poly(ethylene oxide) monomers, poly(propylene oxide) monomers, or poly(ethylene oxide/propylene oxide) monomers. A particularly preferred such monomer is formed from poly(ethylene oxide) and poly(propylene oxide) monomers. They can be random, sequential, or block.

Examples of useful monoethylenically unsaturated poly(alkylene oxide) monomers include, but are not limited to, acrylate-terminated poly(ethylene oxide), methacrylate-terminated poly(ethylene oxide), methoxy poly(ethylene oxide) methacrylate, butoxy poly(ethylene oxide) methacrylate, acrylate-terminated poly(ethylene glycol), methacrylate-terminated poly(ethylene glycol), methoxy poly(ethylene glycol) methacrylate, butoxy poly(ethylene glycol) methacrylate, and combinations thereof. Particularly preferred poly(alkylene oxide) monomers include acrylate and methacrylate esters prepared from mono-hydroxyl-terminated poly(lower alkylene oxides) such as polyethylene and polypropylene glycols commercially available under the trade designation CARBOWAX from Union Carbide Corp. in a variety of molecular weights (e.g., CARBOWAX 350, CARBOWAX 550, CARBOWAX 750, CARBOWAX 2000, and CARBOWAX 5000); and their corresponding alkyloxy-terminated derivatives. Examples of preferred poly(alkylene oxide) monomers include those commercially available under the trade designations SR 256 (2-(2-ethoxyethoxy) ethyl acrylate), CD 550 (methoxy polyethylene glycol (350) monomethacrylate), and CD 552 (methoxy polyethylene glycol (550) monomethacrylate), all of which are available from Sartomer Chemicals, Exton, Pa.; and those commercially available under the trade designations M90G (methoxy polyethylene glycol (about 9 ethyleneoxy units) monomethacrylate) and M230G (methoxy polyethylene glycol (about 23 ethyleneoxy units) monomethacrylate), all of which are available from Shin-Nakamura Chemicals, Wakayama City, Japan. An example of a more preferred poly(alkylene oxide) monomer is methoxy polyethylene glycol (about 9 ethyleneoxy units; MW about 450) monoacrylate, commercially available under the trade designation AM90G from Shin-Nakamura Chemicals. Various combinations of monoethylenically unsaturated poly(alkylene oxide) monomers can be used in the pressure sensitive adhesive polymers of the present invention.

Preferably, the monoethylenically unsaturated poly(alkylene oxide)monomer(s) can be used in an amount of at least about 2 weight percent (wt-%), based on the total weight of the pressure sensitive adhesive polymer. More preferably, the monoethylenically unsaturated poly(alkylene oxide) monomer(s) can be used in an amount of at least about 5 wt-%, based on the total weight of the pressure sensitive adhesive polymer. Preferably, the poly(alkylene oxide) monomer(s) can be used in an amount of no greater than about 30 wt-%, more preferably, no greater than about 25 wt-%, and most preferably, no greater than about 20 wt-%, based on the total weight of the pressure sensitive adhesive polymer.

Nonreactive Poly(Alkylene Oxide) Polymers

One or more nonreactive poly(alkylene oxide) polymers can be combined with the reactive monomers (e.g., (meth)acrylate and reinforcing monomers) or with the copolymer formed from the reactive monomers. A nonreactive poly(alkylene oxide) polymer is selected for use in the pressure sensitive adhesive composition such that it improves the pressure sensitive adhesive characteristics of the copolymerized monomers and is compatible with the copolymerized monomers. As used herein, a compatible component (e.g., a nonreactive polymer or an antimicrobial agent such as chlorhexidine and its aqueous solutions) is one that does not interfere with the polymerization of the monomers and does not phase separate from the adhesive composition or cause phase separation of any component of the adhesive composition.

Also, to maintain adhesion properties, the nonreactive poly(alkylene oxide) polymer remains present and does not significantly evaporate from the adhesive composition. Additionally, the nonreactive poly(alkylene oxide) polymer does not interfere with the polymerization of the (meth)acrylate monomer(s), reinforcing monomer(s), or optional monoethylenically unsaturated poly(alkylene oxide) monomer(s) to form the pressure sensitive adhesives of the present invention. However, if the nonreactive poly(alkylene oxide) polymer is added during polymerization of the reactive monomers, there could be a small amount (typically, less than about 1 wt-%) that copolymerizes with the reactive monomers due to chain transfer. Because this is not a significant amount, the poly(alkylene oxide) polymer is considered "nonreactive."

Thus, a nonreactive poly(alkylene oxide) polymer is a polymer that does not contain free radically reactive ethylenically unsaturated groups that could react with the (meth)acrylate monomers, quaternary ammonium monomers, or poly(alkylene oxide) monomers and does not significantly inhibit the polymerization of these monomers. A poly(alkylene oxide) polymer is preferably a poly(ethylene oxide) polymer, a poly(propylene oxide) polymer, or a poly(ethylene oxide/propylene oxide) polymer. Preferably, the polymer is a poly(ethylene oxide/propylene oxide) polymer formed from ethylene oxide and propylene oxide, which can be in random, sequential, or block form. Particularly useful poly(alkylene oxide) polymers have a weight average molecular weight of about 1000 to about 15,000, preferably of about 3000 to about 12,000.

Preferred nonreactive poly(alkylene oxide) polymers have appreciable water solubility, preferably, at least about 10 parts per 100 parts of water, exhibit surfactant characteristics preferably having an HLB (hydrophilic lipophilic balance) value of about 3 to about 15, and more preferably, about 5 to about 12. Monomers that may be used to make poly(alkylene oxide) polymers include ethylene oxide, propylene oxide, butylene oxide, trimethylene oxide, tetramethylene oxide, and the like, and the corresponding glycols. The poly(alkylene oxide) polymers may be terminated with lower alkyl groups, amino groups, hydroxyl groups, carboxylic acid groups, aromatic groups, or other nonreactive groups.

Examples of useful nonreactive poly(alkylene oxide) polymers include, but are not limited to, those commercially available under the trade designations TETRONIC (tetrafunctional block copolymers derived from sequential addition of propylene oxide and ethylene oxide to ethylene diamine with hydrophilic endblocks) and TETRONIC R (tetrafunctional block copolymers derived from sequential addition of propylene oxide and ethylene oxide to ethylene diamine with hydrophobic endblocks) copolymers, both of which are available from BASF, Mt. Olive, N.J.; PLURONIC (triblock copolymers with poly(ethylene oxide) end blocks and poly(propylene oxide) midblock) and PLURONIC R (triblock copolymers with poly(propylene oxide) endblocks and poly(ethylene oxide) midblocks) copolymers available from BASF; UCON Fluids (random copolymers of ethylene oxide and propylene oxide) available from Union Carbide, Danbury, Conn.; and JEFFAMINE polyalkylene oxide copolymers available from Huntsman Chemical Corp., Houston, Tex. A particularly preferred poly(alkylene oxide) polymer is that commercially available under the trade designation PLURONIC 25R4 (a block copolymer of poly(ethylene oxide) and poly(propylene oxide)) from BASF. Various combinations of polyalkylene oxide copolymers can be used in the pressure sensitive adhesives of the present invention.

Preferably, the poly(alkylene oxide) polymer(s) can be used in an amount of at least about 9 weight percent (wt-%), based on the total weight of the pressure sensitive adhesive composition. More preferably, the poly(alkylene oxide) polymer(s) can be used in an amount of at least about 13 wt-%, and most preferably, at least about 20 wt-%, based on the total weight of the pressure sensitive adhesive composition. Preferably, the poly(alkylene oxide) polymer(s) can be used in an amount of no greater than about 30 wt-%, based on the total weight of the pressure sensitive adhesive composition. The amount of poly(alkylene oxide) polymer(s) used depends upon the type and ratios of the (meth)acrylate monomer(s), reinforcing monomer(s), and poly(alkylene oxide) monomer(s) employed in the polymerizable mixture and the type and molecular weight of the poly(alkylene oxide) polymer(s) used in the pressure sensitive adhesive composition.

Antimicrobial Agents and other Additives

Although the pressure sensitive adhesive composition of the present invention can have antimicrobial activity without any additional antimicrobial agents, additional antimicrobials can be added to the adhesive composition if desired. Suitable additional antimicrobial agents include iodine and its complexed forms such as povidone/iodine, chlorhexidine salts such as chlorhexidine digluconate (CHG), parachlorometaxylenol (PCMX), triclosan, hexachlorophene, fatty acid esters such as glycerol monolaurate, phenols, surfactants having a C12–C22 hydrophobe and a quaternary ammonium group, quaternary amines, quaternary silanes, hydrogen peroxide, phenols, silver, silver salts such as silver chloride, silver oxide, silver sulfadiazine, and the like. In order to reduce chances for irritation and yet maintain efficacy, the antimicrobial level should be adjusted to the minimum level that maintains a low bacteriological count preferably for 6 hours, and more preferably for 12 hours after application.

The most preferred antimicrobial agent is a chlorhexidine salt since it is capable of ensuring long term antimicrobial efficacy. If a chlorhexidine salt is added to the present invention it is preferably present as a soluble salt. The diacetate and digluconate salts are preferred. The most preferred antimicrobial agent is chlorhexidine digluconate (CHG). Various combinations of antimicrobial agents can be used in the pressure sensitive adhesive compositions of the present invention.

Preferably, the antimicrobial agent(s) can be used at a level of at least about 0.05 wt-%, and more preferably, at least about 0.25 wt-%, based on the total weight of the pressure sensitive adhesive composition. Preferably, the antimicrobial agent(s) can be used at a level of no greater than about 15 wt-%, based on the total weight of the pressure sensitive adhesive composition.

Other additives can be included in the polymerizable mixture or added at the time of compounding or coating to change the properties of the adhesive. Such additives include, but are not limited to, pigments, glass or polymeric bubbles or beads (which may be expanded or unexpanded), fibers, reinforcing agents, hydrophobic or hydrophilic silica, toughening agents, fire retardants, antioxidants, crosslinkers, finely ground polymeric particles such as polyester, nylon, and polypropylene, and stabilizers. The additives are added in amounts sufficient to obtain the desired end-use properties.

Polymerization Initiators

A free radical initiator is preferably added to aid in the copolymerization of (meth)acrylates and other monomers. The type of initiator used depends on the polymerization process. Suitable initiators include photoinitiators, thermal initiators, redox initiators, etc. Photoinitiators that are useful for polymerizing the polymerizable mixture of monomers include benzoin ethers such as benzoin methyl ether or benzoin isopropyl ether, substituted benzoin ethers such as 2-methyl-2-hydroxypropiophenone, aromatic sulfonyl chlorides such as 2-naphthalenesulfonyl chloride, and photoactive oxides such as 1-phenyl-1,1-propanedione-2-(O-ethoxycarbonyl)oxime. An example of a commercially available photoinitiator is IRGACURE 651 (2,2-dimethoxy-1,2-diphenylethane-1-one, commercially available from Ciba-Geigy Corp.). Examples of suitable thermal initiators include VAZO-64 (2,2'-azobis(isobutyronitrile)) and VAZO-67 (2,2'-Azobis(2-methylbutanenitrile)), both of which are available from DuPont Co., hydroperoxides, such as tert-butyl hydroperoxide, and peroxides, such as benzoyl peroxide and cyclohexane peroxide. Examples of suitable redox initiators include an oxidizing agent, such as tert-butyl hydroperoxide, and a reducing agent (e.g., tertiary amines, ferrous sulfate, sodium formaldehyde sulfoxylate, and sodium bisulfite). Generally, the initiator is present in an amount of about 0.005 part to about 1 part based on 100 parts of total monomer.

Polymerization Chain Transfer Agents

Optionally, the composition also includes a chain transfer agent to control the molecular weight of the polymerized compositions. Chain transfer agents are materials that regulate free radical polymerization and are generally known in the art. Suitable chain transfer agents include halogenated hydrocarbons such as carbon tetrabromide; sulfur compounds such as lauryl mercaptan, butyl mercaptan, ethanethiol, isooctylthioglycolate (IOTG), 2-ethylhexyl thioglycolate, 2-ethylhexyl mercaptopropionate, 2-mercaptoimidazole, and 2-mercaptoethyl ether, and mixtures thereof. The amount of chain transfer agent that is useful depends upon the desired molecular weight and the type of chain transfer agent. The chain transfer agent is typically used in amounts from about 0.001 part to about 10 parts by weight per 100 parts of total monomer. Alternatively, the solvent (e.g., ethanol, isopropanol) could serve as the chain transfer agent.

Methods of Making Adhesive Compositions

The pressure sensitive adhesives of the present invention can be prepared by a wide variety of conventional free radical polymerization methods, including solution and emulsion polymerizations. Specific polymerization methods used in this invention are discussed in the Examples Section.

In one solution polymerization method, the alkyl (meth) acrylate monomer, reinforcing monomer (preferably, quaternary ammonium monomer), optional poly(allkylene oxide) monomer, and optional nonreactive poly(alkylene oxide) polymer, along with a suitable thermal polymerization initiator, optional chain transfer agent, and solvent are charged into a glass vessel. The reaction vessel is then purged with nitrogen to create an inert atmosphere. Once purged, the solution within the vessel is heated to decompose the added thermal initiator, and the mixture is stirred during the course of the reaction. A conversion of about 98 percent to about 99 percent is typically obtained in about 20 hours. If desired, solvent can be removed to yield a hot melt coatable adhesive. Suitable organic solvents, if required, may be any organic liquid that is miscible with, and inert to, the reactants and product and will not otherwise adversely affect the reaction. Such solvents include methanol, ethanol, acetone, methyl ethyl ketones, and mixtures thereof. The amount of solvent is generally about 30 wt-% to about 80 wt-%, based on the total weight of the reactants and solvents.

The adhesive compositions of the present invention may be applied to a backing by a variety of coating methods, including brush, roll, spray, spread, wire, gravure, transfer roll, air knife, or doctor blade coating. The adhesive composition may also be coated on a release liner and laminated to a suitable backing.

If the composition includes an organic solvent or water, it is then dried at a temperature (e.g., about 65° C. to about 120° C.) and a time (e.g., several minutes to about one hour) so as to provide an adhesive tape or dressing, for example. The thickness of the layer of adhesive may vary over a broad range of about 10 microns to several hundred microns (e.g., about 200 microns).

Once the adhesive composition has been coated, and optionally crosslinked, the adhesive surface of the article may, optionally, be protected with a temporary, removable release liner (i.e., protective liner) such as a polyolefin (e.g., polyethylene or polypropylene) or polyester (e.g., polyethylene terephthalate) film, or a plastic film. Such films may be treated with a release material such as silicones, waxes, fluorocarbons, and the like.

Backings and Articles

The pressure sensitive adhesives of the present invention that adhere to skin and similar surfaces are useful in many medical applications. For example, these pressure sensitive adhesives are useful in medical applications, such as tapes, bandages, dressings, and drapes (e.g., incise drapes) to adhere to moist skin surfaces.

The adhesive compositions can be included in a variety of dressing constructions known in the art. Typically, the composition is in the form of a continuous or discontinuous coating on at least one major surface of a backing. The backing may include one or more layers and be in a variety of forms (e.g., foams or films). Examples of suitable backings include materials with a relatively low content of hydrophilic components such as polyester (e.g., commercially available under the trade designation HYTREL, such as HYTREL 4056, from DuPont Co.), polyurethane (e.g., commercially available under the trade designation ESTANE, such as ESTANE 58309 and ESTANE 58237, from B.F. Goodrich Co.), polyether block amide (e.g., commercially available under the trade designation PEBAX, such as PEBAX 2533 and 3533, (Atofina Chemicals, Inc., Philadelphia, Pa.), and porous polyethylene resins. Also suitable are materials having relatively high moisture vapor transmission properties. Examples include certain polyether amides such as that commercially available under the trade designation PEBAX 4011RN00 from Atofina Chemicals, Inc., and polyurethanes as described in U.S. Pat. No. 4,598,004 (Heinecke). Both classes of materials may also be used in combination with each other (e.g., in sandwich-type arrangements) to tailor the moisture vapor transmission properties of the dressing. Examples of specific dressing configurations for which the compositions are suitable are described in U.S. Pat. No. 4,952,618 (Olsen).

EXAMPLES

The objects, features, and advantages of the present invention illustrated in the following examples, which incorporate particular materials and amounts, should not be construed to unduly limit this invention. All materials are commercially available unless otherwise stated or apparent. All parts, percentages, ratios, etc., in the examples are by weight unless otherwise indicated.

| | Glossary | |
|---|---|---|
| EHA | 2-Ethylhexyl acrylate | BASF, Mt. Olive, NJ |
| AA | Acrylic acid | BASF, Mt. Olive, NJ |
| BA | Butyl acrylate | Hoechst Celanese, Dallas, TX |
| AM90G | Methoxy(polyethylene oxide) acrylate (approximately 450 MW) | Shin-Nakamura Chemicals, Wakayama City, Japan |
| DMAEAMC | Dimethylaminoethyl acrylate methyl chloride quaternary salt (Ageflex FA1Q80MC); 80% aqueous solution | Ciba Specialty Chemicals, Woodbridge, NJ |
| DMAEAMS | Dimethylaminoethyl acrylate dimethyl sulfate quaternary salt (Ageflex FA1Q80DMS); 80% aqueous solution | Ciba Specialty Chemicals, Woodbridge, NJ |
| C16-MA | Dimethylaminoethyl methacrylate hexadecyl bromide quaternary salt | Prepared as described in Example 1 of U.S. Pat. No. 5,437,932 (Ali et al.) |
| PLURONIC 25R4 | Block copolymer of poly(ethylene oxide) and poly(propylene oxide) | BASF, Mt. Olive, NJ |
| CHG | Chlorhexidine gluconate (20% aqueous solution) | Xttrium Labs, Chicago, IL |
| TBA | Tertiary butyl alcohol | Sigma-Aldrich Fine Chemicals, St. Louis, MO |
| VAZO-67 | 2,2'-Azobis(2-methylbutanenitrile) | Dupont, Wilmington, DE |

Test Protocols

Inherent Viscosity (IV)

The inherent viscosity of a polymer is measured in accordance with the protocol described by Fred Bilmeyer, Jr. at pages 84–85 of the textbook entitled *Textbook of Polymer Science*, Second Edition, published by Wiley-Interscience (1971). Briefly, solution viscosity is measured by comparing the efflux time (t) required for a specified volume of polymer solution to flow through a capillary tube with the corresponding efflux time ($t_0$) for the solvent. The measured variables t, $t_0$, and solute concentration (c) are then used to calculate inherent viscosity (also know as Logarithmic Viscosity) using the equation:

$$\eta = (\ln t/t_0)/c$$

For the examples of the present invention, IV was determined as a 0.15 to 0.50 weight percent solution of the pressure sensitive adhesive polymer in tetrahydrofuran (THF).

Moisture Vapor Transmission Rate (MVTR)

MVTR, was evaluated in a manner analogous to that described in ASTM E 96-80 at 40° C. and 80% relative humidity (RH) difference and expressed in grams transmitted per square meter per day ($g/m^2/24$ hr). An adhesive tape sample should exhibit an MVTR value of not less than 500 $g/m^2/24$ hr to be considered permeable to water vapor.

Peel Adhesion to Glass

The peel adhesion method was used to measure the force required to remove an adhesive sample from a test substrate surface at a specific angle and rate of removal. The room temperature peel adhesion was measured at 21° C. and 50% RH against a clean glass plate. A tape sample (1.27-cm wide×20-cm long) was adhered to the glass plate using one pass of 2. 1-kg rubber-faced roller and tested using a Model 3M90 Slip/Peel tester (IMASS, Inc., Accord, Mass.) at an angle of 180° and a rate of 229 cm/min. Two replicas were run and an average result was recorded in ounces/inch (oz/in) and converted to Newtons per decimeter (N/dm).

Shear to Stainless Steel

Shear strength, as determined by holding time, was measured for adhesive samples against a clean stainless steel substrate. A tape sample (1.27-cm wide×20-cm long) was conditioned for greater than 24 hours at approximately 21° C. and 50% RH and adhered to the steel substrate surface using four passes of a 2.1-kilogram (kg) rubber-faced roller. The substrate was placed in a vertical holding rack, a static 500-gram (g) load was attached to the end of the sample at an angle of 180°, and the time for the load to drop was measured in minutes. For those samples still adhering to the substrate after 10,000 minutes, the test was discontinued. Two replicas were run and an average result was recorded in minutes.

Adhesion to Dry and Wet Skin

Evaluation of the adhesiveness of a composition to human skin is an inherently temperamental determination. Human skin possesses wide variations in composition, topography, and the presence/absence of various body fluids. However, comparative average values of tape or dressing adhesion are attainable by using test results from several individuals as described herein.

Initial skin adhesion ($T_0$) to dry or wet skin and skin adhesion at 24 hours ($T_{24}$) or 48 hours ($T_{48}$) were was measured in accordance with the widely accepted PSTC-1 Peel Adhesion Test (incorporated herein by reference), a testing protocol established by the Specifications and Technical Committee of the Pressure-Sensitive Tape Council located at 5700 Old Orchard Road, Skokie, Ill. The test was modified for the purposes of this invention by applying the dressing sample to the skin of a living human.

Three samples (one for $T_0$ wet-skin testing, one for $T_0$ dry-skin testing, and one for $T_{24}$ or $T_{48}$ dry skin testing), each measuring 2.5-cm wide by 7.5-cm long, were applied to the back of each of one to two human subjects. The subjects were placed in a prone position with arms at their sides and heads turned to one side. Samples were applied without tension or pulling of skin to both sides of the spinal column with the length of each sample positioned at a right angle to the spinal column.

Those samples tested for wet skin adhesion were applied to skin which had been moistened with a water saturated cloth, leaving visually observable drops of standing water, immediately before application of the sample.

The samples were pressed into place with a 2-kg roller moved at a rate of approximately 2.5 cm/sec with a single forward and reverse pass. No manual pressure was applied to the roller during application.

The samples were then removed immediately after application ($T_0$) at a removal angle of 180° and at a removal rate of 15 centimeters per minute (cm/min) using a conventional adhesion tester equipped with a 11.3 kg test line attached to a 2.5 cm clip. The clip was attached to the edge of the sample furthest from the spinal column by manually lifting about 1 cm of the sample from the skin and attaching the clip to the raised edge. The adhesion tester was a strain-gauge mounted on a motor-driven carriage. The measured force required to effect removal of each dressing sample was reported (as an average of 6–16 sample replications) in grams/inch and converted to Newtons per decimeter (N/dm). Preferably, to adhere to wet skin, the ($T_0$) wet value is at least about 0.8 N/dm and it is desired that the ($T_0$) wet value is approximately the same as the ($T_0$) dry value.

Antimicrobial Activity

A test adhesive dressing of the present invention (Test Sample) or a control/placebo adhesive dressing (Placebo Sample; prepared by coating PSA microspheres without added antimicrobial agent, as described in Example 1 of U.S. Pat. No. 5,614,310 (Delgado et al.), on a transparent polyurethane backing) was brought into contact with a known population of microorganisms for a specified period of time at a specified temperature. At the end of the designated time period, the activity of the Test or Placebo Sample was neutralized and surviving microorganisms enumerated by plate count methods. The $\log_{10}$ reduction was calculated by subtracting $\log_{10}$ CFU/ml of organisms recovered from the Test Sample from the Placebo Sample $\log_{10}$ CFU/ml recovery.

Preparation of Inoculum. An inoculum suspension of *Staphylococcus epidermidis* (ATTC # 12228) was prepared in sterile Butterfield's phosphate buffered water (Hardy Diagnostics, Santa Maria, Calif.) at a concentration of approximately $5 \times 10^8$ CFU/ml.

Preparation of Test and Placebo Samples. The Test and Placebo Samples were prepared in duplicate on the same day of testing. Samples were aseptically die-cut into 2.5-cm diameter circles and aseptically transferred to individual sterile Petri-dishes. The liner was aseptically removed from the sample, exposing the adhesive area.

Test Procedure. The adhesive side of the Test (or Placebo) Sample was inoculated with 50 $\mu$l of the bacterial inoculum suspension. The suspension was administered in tiny droplets (no less than 15) over the entire adhesive area. The samples were incubated at 35+/−2° C. for 30 minutes (timing started at contact with total inoculum suspension volume). Following incubation, each sample was transferred to a centrifuge tube containing 25 milliliters (ml) of a buffer with neutralizers, vortexed for 2 minutes (min), sonicated for 5 minutes and then vortexed again for 2 minutes. The samples were serially diluted in Butterfield's phosphate buffered water and pour-plated with Trypticase Soy Agar (Difco, Detroit, Mich.). Plates were incubated at 35+/−2° C. for 48 hours (hr, colonies were counted and data converted to $\log_{10}$ CFU/ml. Log reductions were calculated by subtracting the $\log_{10}$ bacterial recovery of the Test Samples from the $\log_{10}$ bacterial recovery of the Placebo Samples. Results are reported as the average of duplicate samples.

Examples 1–5

Polymer Preparations

A PSA Polymer Solution was Prepared by the Following Procedure:

Butyl acrylate (112.5 g), DMAEAMC (37.5 g), AM90G (7.5 g) (75/20/5, respectively, weight ratio), 95% ethanol (105 g), and VAZO 67 radical initiator (0.75 g) were mixed together in a glass bottle. The bottle was degassed with nitrogen, sealed, and heated in a water bath at 57° C. for 24 hours. After cooling to room temperature, the resulting polymer solution was clear in appearance. Small samples were taken to measure molecular weight, monomer conversions and other polymer or polymerization related properties. Additives, such as CHG solution, would be added at this stage by direct mixing, if needed. These solutions were then coated onto suitable substrates as described in subsequent examples.

Additional polymer solutions were prepared in a similar manner except that different weight ratios of the three monomers were used. In all cases (Examples 1–5), monomer conversion (determined by percent solids measured by loss on drying at 105° C. for 3 hours) was essentially complete at 24 hours (greater than 98%) and the polymer solutions contained 57% solids. Samples of the polymer solutions were used to measure inherent viscosity (IV) and the values are shown in Table 1.

TABLE 1

| Example | Monomer Weight Ratios | | | IV (0.25 g in THF) |
|---|---|---|---|---|
| | BA | DMAEAMC | AM-90G | |
| 1 | 75 | 20 | 5 | 0.14 |
| 2 | 78 | 20 | 2 | 0.13 |
| 3 | 80 | 20 | 0 | 0.11 |
| 4 | 70 | 25 | 5 | 0.09 |
| 5 | 73 | 25 | 2 | 0.14 |

Examples 6–22

Polymer Preparations

PSA polymer solutions were prepared as described in Examples 1–5, except that BA was replaced by EHA. The ratios of monomers used, reaction temperatures, and the percent solids are shown in Table 2. In the case of Example 22, the 95% ethanol solvent was replaced by a 2/1 (weight ratio) of acetone/methanol. After cooling to room temperature, all of the polymer solutions were clear in appearance.

TABLE 2

| Example | Monomer Weight Ratios | | | Reaction Temp, ° C. | Percent Solids |
|---|---|---|---|---|---|
| | EHA | DMAEAMC | AM90G | | |
| 6 | 70 | 20 | 10 | 57 | 50 |
| 7 | 65 | 15 | 10 | 57 | 50 |
| 8 | 75 | 20 | 5 | 57 | 50 |
| 9 | 78 | 20 | 2 | 57 | 50 |
| 10 | 70 | 25 | 5 | 57 | 50 |
| 11 | 73 | 25 | 2 | 57 | 50 |
| 12 | 85 | 10 | 5 | 60 | 60 |
| 13 | 80 | 10 | 10 | 60 | 60 |
| 14 | 82.5 | 15 | 2.5 | 60 | 60 |
| 15 | 80 | 15 | 5 | 60 | 60 |
| 16 | 75 | 15 | 10 | 60 | 60 |
| 17 | 77.5 | 20 | 2.5 | 60 | 60 |
| 18 | 75 | 20 | 5 | 60 | 60 |
| 19 | 70 | 20 | 10 | 60 | 60 |
| 20 | 70 | 25 | 5 | 60 | 60 |
| 21 | 65 | 25 | 10 | 60 | 60 |
| 22 | 75 | 20 | 5 | 60 | 45 |

Examples 23–26

Polymer Preparations

PSA polymer solutions were prepared as described in Examples 1–5, except that different monomers were used as shown in Table 3. Also shown in this table are percent monomer conversions and IV values. After cooling to room temperature, all of the polymer solutions were clear in appearance.

TABLE 3

| Ex. | Monomer Weight Ratios | | | | Conversion Percent | IV (0.15 g in THF) |
|---|---|---|---|---|---|---|
| | EHA | DMAEAMC | C16-MA | AA | | |
| 23 | 85 | 0 | 10 | 5 | 98.3 | 1.01 |
| 24 | 80 | 0 | 20 | 0 | 96.9 | 0.79 |
| 25 | 85 | 10 | 0 | 5 | 98.5 | 0.61 |
| 26 | 80 | 20 | 0 | 0 | 97.9 | 0.22 |

Examples 27–49

Polymer Preparations

PSA polymer solutions were prepared as described in Examples 1–5, except that DMAEAMC was replaced by DMAEAMS, and various solvents were used. The reaction temperature was either 60° C. (Examples 27–46) or 58° C. (Examples 47–49). The ratios of monomers used, solvents, percent solids, percent monomer conversions, and IV values are shown in Table 4. After cooling to room temperature, all of the polymer solutions were clear in appearance except for Examples 38, 39, and 41–45 that were slightly hazy.

TABLE 4

| Ex. | Monomer Weight Ratios | | | Solvent Ac = Acetone (Weight Ratios) | Percent Solids | Conv. Percent | IV (0.50 g in THF) |
|---|---|---|---|---|---|---|---|
| | EHA | DMAEAMS | AM90G | | | | |
| 27 | 75 | 20 | 5 | 95% Ethanol | 50 | ND[1] | ND |
| 28 | 70 | 25 | 5 | 95% Ethanol | 50 | ND | ND |
| 29 | 75 | 20 | 5 | 95% Ethanol | 40 | ND | ND |
| 30 | 70 | 25 | 5 | 95% Ethanol | 40 | ND | ND |
| 31 | 65 | 30 | 5 | 95% Ethanol | 40 | ND | ND |
| 32 | 75 | 20 | 5 | Ac/Methanol (2.2/1) | 40 | ND | ND |
| 33 | 70 | 25 | 5 | Ac/Methanol (2.2/1) | 40 | ND | ND |
| 34 | 75 | 20 | 5 | 95% Ethanol | 40 | 98.7 | 0.14 |
| 35 | 70 | 25 | 5 | 95% Ethanol | 43 | 98.2 | 0.13 |
| 36 | 75 | 20 | 5 | Ac/Methanol (2.2/1) | 40 | 98.2 | 0.29 |
| 37 | 70 | 25 | 5 | Ac/Methanol (2.2/1) | 45 | 97.2 | 0.20 |
| 38 | 83 | 15 | 2 | Ac/Ethanol (3/1) | 45 | ND | ND |
| 39 | 80 | 15 | 5 | Ac/Ethanol (3/1) | 45 | ND | ND |
| 40 | 75 | 15 | 10 | Ac/Ethanol (3/1) | 45 | ND | ND |
| 41 | 78 | 20 | 2 | Ac/Ethanol (2.5/1) | 45 | ND | ND |
| 42 | 75 | 20 | 5 | Ac/Ethanol (2.5/1) | 45 | ND | ND |
| 43 | 70 | 20 | 10 | Ac/Ethanol (2.5/1) | 45 | ND | ND |
| 44 | 73 | 25 | 2 | Ac/Ethanol (2.2/1) | 45 | ND | ND |
| 45 | 70 | 25 | 5 | Ac/Ethanol (2.2/1) | 45 | ND | ND |
| 46 | 65 | 25 | 10 | Ac/Ethanol (2.2/1) | 45 | ND | ND |
| 47 | 65 | 15 | 20 | Ac/Methanol (3/1) | 45 | 99.5 | 0.51 |
| 48 | 70 | 15 | 15 | Ac/Methanol (3/1) | 45 | 97.9 | 0.50 |
| 49 | 75 | 10 | 15 | Ac/Methanol (3/1) | 45 | 100 | 0.69 |

[1]ND = Not Determined

Examples 50–51

Polymer Preparations

PSA polymer solutions were prepared as described in Examples 1–5, except that BA was replaced by EHA, DMAEAMC was replaced by DMAEAMS, AM90G was replaced by the block copolymer PLURONIC 25R4, and the 95% ethanol solvent was replaced by 3.9/1 acetone/methanol. The reaction temperature was 60° C. and the percent solids (before added solvent) was 40%. The ratios of monomers/25R4 used, solvents, and percent solids (after added solvent) are shown in Table 5. Both examples showed phase separation after polymerization, and the added solvent was required to provide a clear polymer solution.

TABLE 5

| Ex. | Component Weight Ratios | | | Added Solvent | Percent Solids (After Added Solvent) |
|---|---|---|---|---|---|
| | EHA | DMAEAMS | PLURONIC 25R4 | | |
| 50 | 75 | 15 | 10 | Acetone (10 g) | 33.3 |
| 51 | 80 | 10 | 10 | Acetone (15 g) Methanol (5 g) | 28.6 |

Examples 52–59

Polymer Plus CHG Preparations

PSA polymer solutions were prepared as described in Examples 27–49 using 2.5/1 acetone/ethanol as the solvent. The reaction temperature was 60° C. and the percent solids was 45%. After cooling to room temperature, the polymer solutions were clear in appearance. Following the polymerization reaction, CHG antimicrobial (20% aqueous solution) was added to the cooled polymer solutions such that the resulting polymer consisted of 98% polymer solids and 2% CHG (100% basis) (Examples 53 and 56) or 95% polymer solids and 5% CHG (100% basis) (Examples 54 and 57). In a similar manner, CHG (20% solution) was added to the polymer solution (Example 35) in an amount of 2% (Example 58) and in amount of 5% (Example 59). The final solutions were generally clear, colorless, and stable. The ratios of monomers used, added CHG, percent monomer conversions, and IV values are shown in Table 6.

TABLE 6

| Ex. | Monomer Weight Ratios | | | Added CHG (Wt. %) | Conv. Percent | IV (0.50 g in THF) |
|---|---|---|---|---|---|---|
| | EHA | DMAEAMS | AM90G | | | |
| 52 | 75 | 20 | 5 | 0 | 98.0 | 0.37 |
| 53 | 75 | 20 | 5 | 2 | ND[1] | ND |
| 54 | 75 | 20 | 5 | 5 | ND | ND |
| 55 | 70 | 25 | 5 | 0 | 98.5 | 0.31 |
| 56 | 70 | 25 | 5 | 2 | ND | ND |
| 57 | 70 | 25 | 5 | 5 | ND | ND |
| 58 | 70 | 25 | 5 | 2 | ND | ND |
| 59 | 70 | 25 | 5 | 5 | ND | ND |

[1]ND = Not Determined

Examples 60–97

Preparation of Backings Having a PSA Polymer Layer

Laminates. Backing/PSA laminates were prepared by the following procedure. A PSA polymer solution was coated onto a silicone-coated liner (POLYSLIK S-8004, Rexam Release, Inc., Bedford Park, Ill.) with a knife-over-bar coater and dried in an air-circulating oven at 100° C. for 10 minutes to provide a 1-mil (0.025 mm) dried adhesive film. The adhesive film was then laminated to a 1-mil (0.025 mm) thick film of ESTANE 58309 or ESTANE 58237 polyurethane (B. F. Goodrich, Cleveland, Ohio). The resulting laminates (Examples 60–93) were then cut into circles (3.5-cm diameter) for evaluation of MVTR; strips (12.7-cm×20-cm) for evaluation of peel adhesion and shear; and strips (2.5-cm×7.5-cm) for evaluation of skin adhesion. The strips used for skin adhesion were sterilized with gamma radiation at 32–36 kGy. Evaluation results are provided in Tables 7 and 8.

Coated Backings. PSA-coated backings were prepared by the following procedure. A PSA polymer solution was coated onto a 2-mil (0.05 mm) polyester (PET) film (3M SCOTCHPAR PET film, 1.97 mil P0870197, 3M Company, St. Paul, Minn.) with a knife-over-bar coater and dried in an air-circulating oven at 100° C. for 10 minutes to provide a 1-mil (0.025 mm) dried adhesive film. The resulting PSA-coated films (Examples 94–97) were then cut into circles (2.5-cm diameter) for evaluation of antimicrobial activity. Evaluation results are shown in Table 9.

Evaluations and Results

MVTR

Examples 60–64 (PSA Examples 1–5 laminated to a polyurethane film backing) were evaluated for MVTR according to the test method provided herein and the results are provided in Table 7. It is concluded from these data that the laminates constructed from a polyurethane film and PSAs composed of BA/DMAEAMC/AM90G copolymers show good permeability to water vapor.

Peel Adhesion and Shear Data

Examples 65–69 (PSA Examples 22–26 laminated to a polyurethane film backing) were evaluated for Peel Adhesion on Glass and Shear on stainless steel according to the test method provided herein and the results are provided in Table 7. It is concluded from these data that, in copolymers with EHA, DMAEAMC is a more powerful reinforcing monomer than C 16-MA and that it can be used with or without other reinforcing monomers (such as AA) to make PSAs with good adhesive properties.

TABLE 7

| PSA Example | Example | MVTR g/m²/24 hr | Peel Adhesion oz/in | Peel Adhesion N/dm | Shear minutes |
|---|---|---|---|---|---|
| 60 | 1 | 4360 | ND[1] | ND | ND |
| 61 | 2 | 2260 | ND | ND | ND |
| 62 | 3 | 2280 | ND | ND | ND |
| 63 | 4 | 2950 | ND | ND | ND |
| 64 | 5 | 2860 | ND | ND | ND |
| 65 | 22 | ND | 28.0 | 30.6 | 1613 |
| 66 | 23 | ND | 63.3 | 69.3 | 73 |
| 67 | 24 | ND | 64.6 | 70.8 | 244 |
| 68 | 25 | ND | 45.3 | 49.6 | >10,000 |
| 69 | 26 | ND | 34.3 | 37.6 | >10,000 |

ND[1] = Not Determined

Adhesion to Skin

Examples 70–93 (PSA Examples 1–5, 8–11, 38–46, and 52–57 laminated to a polyurethane film backing) were evaluated for adhesion to skin according to the test method provided herein and the results are provided in Table 8 along with results from a commercial PSA medical tape (TEGADERM, 3M Company, St. Paul, Minn.). It is concluded from the results of Table 8 that all backing-plus-PSA Examples had good wet and initial dry skin adhesion values (greater than 0.8 N/dm) and that all Examples had an initial wet skin adhesion of at least 65% of the initial dry skin adhesion.

TABLE 8

| Example | PSA Example | $T_0$ Dry g/inch | $T_0$ Dry N/dm | $T_0$ Wet g/inch | $T_0$ Wet N/dm | $T_{48}$ Dry g/inch | $T_{48}$ Dry N/dm |
|---|---|---|---|---|---|---|---|
| 70 | 1 | 52 | 2.01 | 113 | 4.35 | 134 | 5.18 |
| 71 | 2 | 41 | 1.57 | 70 | 2.71 | 129 | 4.97 |
| 72 | 3 | 47 | 1.80 | 100 | 3.87 | 128 | 4.95 |
| 73 | 4 | 67 | 2.59 | 124 | 4.78 | 127 | 4.89 |
| 74 | 5 | 62 | 2.40 | 102 | 3.93 | 125 | 4.84 |
| TEGADERM | | 84 | 3.23 | 43 | 1.64 | 131 | 5.07 |
| 75 | 8 | 73 | 2.82 | 65 | 2.50 | 129 | 4.99 |
| 76 | 9 | 98 | 3.77 | 93 | 3.60 | 125 | 4.81 |
| 77 | 10 | 83 | 3.19 | 89 | 3.44 | 116 | 4.47 |
| 78 | 11 | 71 | 2.75 | 61 | 2.37 | 117 | 4.51 |
| TEGADERM | | 51 | 1.96 | 58 | 2.24 | 128 | 4.93 |
| 79 | 38 | 30 | 1.15 | 30 | 1.14 | 125 | 4.83 |
| 80 | 39 | 32 | 1.23 | 37 | 1.45 | 133 | 5.12 |
| 81 | 40 | 53 | 2.06 | 47 | 1.81 | 158 | 6.12 |
| 82 | 41 | 21 | 0.81 | 29 | 1.11 | 104 | 4.02 |
| 83 | 42 | 32 | 1.23 | 45 | 1.75 | 130 | 5.02 |
| 84 | 43 | 44 | 1.69 | 54 | 2.07 | 154 | 5.93 |
| 85 | 44 | 19 | 0.71 | 26 | 0.99 | 99 | 3.81 |
| 86 | 45 | 26 | 1.01 | 32 | 1.25 | 123 | 4.76 |
| 87 | 46 | 36 | 1.37 | 50 | 1.92 | 160 | 6.19 |
| 88 | 52 | 77 | 2.97 | 55 | 2.12 | 316 | 12.20 |
| 89 | 53 | 76 | 2.93 | 63 | 2.43 | 289 | 11.16 |
| 90 | 54 | 73 | 2.82 | 75 | 2.90 | 375 | 14.48 |
| 91 | 55 | 78 | 3.01 | 57 | 2.20 | 289 | 11.16 |
| 92 | 56 | 97 | 3.75 | 64 | 2.47 | 313 | 12.08 |
| 93 | 57 | 80 | 3.09 | 63 | 2.43 | 320 | 12.35 |
| TEGADERM | | 79 | 3.05 | 68 | 2.63 | 155 | 5.98 |

Antimicrobial Activity

Examples 94–97 (PSA Examples 34–35 and 58–59 coated on a polyester film backing) were evaluated for antimicrobial activity according to the test method provided herein and the results are provided in Table 9. It is concluded from the results of Table 9 that the two Examples of Backing-plus-PSA having no added CHG (Examples 94 and 95) demonstrated antimicrobial activity against *Staphylococcus epidermidis* (1.06 and 3.55 $\log_{10}$ reductions) compared to the Placebo Sample. The data also indicated that the test adhesive dressings containing 2 and 5% CHG (Examples 96 and 97) had increased antimicrobial activity with observed $\log_{10}$ reductions of 4.64 and 6.04 respectively.

TABLE 9

| Example | PSA Example | Added CHG (%) | Reduction in CFU (Decimal Log) |
| --- | --- | --- | --- |
| 94 | 34 | 0 | 1.06 |
| 95 | 35 | 0 | 3.55 |
| 96 | 58 | 2 | 4.64 |
| 97 | 59 | 5 | 6.04 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A pressure sensitive adhesive composition comprising a pressure sensitive adhesive polymer comprising:
   at least one copolymerized monoethylenically unsaturated (meth)acrylic acid ester monomer, wherein the (meth) acrylic acid ester monomer, when homopolymerized, has a Tg of less than about 25° C.;
   at least one copolymerized monoethylenically unsaturated reinforcing monomer, wherein the reinforcing monomer, when homopolymerized, has a Tg of at least about 25° C.; and
   at least one copolymerized poly(alkylene oxide) (meth) acrylic acid ester monomer;
   wherein the pressure sensitive adhesive polymer is functionalized with quaternary ammonium functional groups, and further wherein the quaternary ammonium functional groups are covalently bonded to the polymer.

2. The pressure sensitive adhesive composition of claim 1 further comprising at least one nonreactive poly(alkylene oxide) polymer.

3. The pressure sensitive composition of claim 2 wherein the nonreactive poly(alkylene oxide) polymer comprises copolymerized monomers selected from the group consisting of ethylene oxide, propylene oxide, butylene oxide, trimethylene oxide, tetramethylene oxide, their corresponding glycols, and mixtures thereof.

4. The pressure sensitive adhesive composition of claim 1 wherein the pressure sensitive adhesive polymer has a Tg of no greater than about 10° C.

5. The pressure sensitive adhesive composition of claim 4 wherein the pressure sensitive adhesive polymer has a Tg of no greater than about –10° C.

6. The pressure sensitive adhesive composition of claim 5 wherein the pressure sensitive adhesive polymer has a Tg of no greater than about –20° C.

7. The pressure sensitive adhesive composition of claim 1 wherein the pressure sensitive adhesive polymer is inherently antimicrobial.

8. The pressure sensitive adhesive composition of claim 1 further comprising at least one antimicrobial agent.

9. The pressure sensitive adhesive composition of claim 8 wherein the antimicrobial agent is present in an amount of at least about 0.05 wt-%, based on the total weight of the pressure sensitive adhesive composition.

10. The pressure sensitive adhesive composition of claim 8 wherein the antimicrobial agent is selected from the group consisting of iodine, complexed forms of iodine, chlorhexidine salts, parachlorometaxylenol, triclosan, hexachlorophene, fatty acid esters, phenols, surfactants having a C12–C22 hydrophobe and a quaternary ammonium group, quaternary amines, quaternary silanes, hydrogen peroxide, silver, silver salts, silver oxide, silver sulfadiazine, and combinations thereof.

11. The pressure sensitive adhesive composition of claim 10 wherein the antimicrobial agent is a chlorhexidine salt.

12. The pressure sensitive adhesive composition of claim 1 wherein the monoethylenically unsaturated reinforcing monomer is a quaternary ammonium monomer.

13. An article comprising a backing and the pressure sensitive adhesive composition of claim 1 on at least a portion of a surface thereof.

14. The article of claim 13 which adheres to wet skin.

15. The article of claim 14 which has an initial wet skin adhesion of at least about 0.8 N/dm.

16. The article of claim 15 which has an initial wet skin adhesion of at least about 1.6 N/dm.

17. The article of claim 14 which has an initial dry skin adhesion of at least about 0.8 N/dm.

18. The article of claim 14 which has an initial wet skin adhesion that is at least about 65% of the initial dry skin adhesion.

19. The article of claim 13 which is a medical article.

20. A method of using an adhesive article, the method comprising:
   providing an adhesive article comprising a backing and the pressure sensitive adhesive composition of claim 1 disposed on at least a portion of a surface thereof; and
   adhering the adhesive article to skin.

21. A pressure sensitive adhesive composition comprising a pressure sensitive adhesive polymer comprising:
   at least one copolymerized monoethylenically unsaturated (meth)acrylic acid ester monomer, wherein the (meth) acrylic acid ester monomer, when homopolymerized, has a Tg of less than about 25° C.; and
   at least one copolymerized monoethylenically unsaturated reinforcing monomer, wherein the reinforcing monomer, when homopolymerized, has a Tg of at least about 25° C.;
   at least one copolymerized poly(alkylene oxide) (meth) acrylic acid ester monomer;
   wherein the pressure sensitive adhesive polymer is functionalized with quaternary ammonium functional groups;
   wherein the quaternary ammonium functional groups are covalently bonded to the polymer; and further wherein the pressure sensitive adhesive composition adheres to wet skin.

22. A method of using an adhesive article, the method comprising:
providing an adhesive article comprising a backing and the pressure sensitive adhesive composition of claim 21 disposed on at least a portion of a surface thereof; and
adhering the adhesive article to skin.

23. An article comprising a backing and the pressure sensitive adhesive composition of claim 21 on at least a portion of a surface thereof.

24. A pressure sensitive adhesive composition comprising a pressure sensitive adhesive polymer comprising:
at least one copolymerized monoethylenically unsaturated (meth)acrylic acid ester monomer, wherein the (meth)acrylic acid ester monomer, when homopolymerized, has a Tg of less than about 25° C.;
at least one copolymerized quaternary ammonium monomer, wherein the quaternary ammonium monomer, when homopolymerized, has a Tg of at least about 25° C.; and
at least one copolymerized poly(alkylene oxide) (meth)acrylic acid ester monomer;
wherein the pressure sensitive adhesive polymer is functionalized with quaternary ammonium functional groups, and further wherein the quaternary ammonium functional groups are covalently bonded to the polymer.

25. The pressure sensitive adhesive composition of claim 24 further comprising at least one nonreactive poly(alkylene oxide) polymer.

26. The pressure sensitive adhesive composition of claim 24 wherein the pressure sensitive adhesive is inherently antimicrobial.

27. An article comprising a backing and the pressure sensitive adhesive composition of claim 24 disposed on at least a portion of a surface thereof.

28. A method of using an adhesive article, the method comprising:
providing an adhesive article comprising a backing and the pressure sensitive adhesive composition of claim 24 disposed on at least a portion of a surface thereof; and
adhering the adhesive article to skin.

29. A pressure sensitive adhesive composition comprising:
at least one antimicrobial agent;
at least one nonreactive poly(alkylene oxide) polymer; and
a pressure sensitive adhesive polymer comprising:
at least one copolymerized monoethylenically unsaturated (meth)acrylic acid ester monomer, wherein the (meth)acrylic acid ester monomer, when homopolymerized, has a Tg of less than about 25° C.;
at least one copolymerized quaternary ammonium monomer, wherein the quaternary ammonium monomer, when homopolymerized, has a Tg of at least about 25° C.; and
at least one copolymerized poly(alkylene oxide) (meth)acrylic acid ester monomer;
wherein the pressure sensitive adhesive polymer is functionalized with quaternary ammonium functional groups, and further wherein the quaternary ammonium functional groups are covalently bonded to the polymer.

30. An article comprising a backing and the pressure sensitive adhesive composition of claim 29 disposed on at least a portion of a surface thereof.

31. A method of using an adhesive article, the method comprising:
providing an adhesive article comprising a backing and the pressure sensitive adhesive composition of claim 29 disposed on at least a portion of a surface thereof; and
adhering the adhesive article to skin.

32. A pressure sensitive adhesive composition comprising a pressure sensitive adhesive polymer comprising:
at least one copolymerized monoethylenically unsaturated (meth)acrylic acid ester monomer, wherein the (meth)acrylic acid ester monomer, when homopolymerized, has a Tg of less than about 25° C.;
at least one copolymerized monoethylenically unsaturated reinforcing monomer, wherein the reinforcing monomer, when homopolymerized, has a Tg of at least about 25° C.; and
at least one copolymerized poly(alkylene oxide) (meth)acrylic acid ester monomer;
wherein the pressure sensitive adhesive polymer is functionalized with quaternary ammonium functional groups, and further wherein the quaternary ammonium functional groups are covalently bonded to the polymer; and further wherein the pressure sensitive adhesive polymer includes no more than about 5 weight percent of copolymerized acidic monomers, based on the total weight of pressure sensitive adhesive polymer.

33. An article comprising a backing and the pressure sensitive adhesive composition of claim 32 disposed on at least a portion of a surface thereof.

34. A method of using an adhesive article, the method comprising:
providing an adhesive article comprising a backing and the pressure sensitive adhesive composition of claim 32 disposed on at least a portion of a surface thereof; and
adhering the adhesive article to skin.

35. A pressure sensitive adhesive composition comprising:
at least one antimicrobial agent; and
a pressure sensitive adhesive polymer comprising:
at least one copolymerized monoethylenically unsaturated (meth)acrylic acid ester monomer, wherein the (meth)acrylic acid ester monomer, when homopolymerized, has a Tg of less than about 25° C.;
at least one copolymerized quaternary ammonium monomer, wherein the quaternary ammonium monomer, when homopolymerized, has a Tg of at least about 25° C.; and
at least one copolymerized poly(alkylene oxide) (meth)acrylic acid ester monomer;
wherein the pressure sensitive adhesive polymer is functionalized with quaternary ammonium functional groups, and further wherein the quaternary ammonium functional groups are covalently bonded to the polymer.

36. An article comprising a backing and the pressure sensitive adhesive composition of claim 35 disposed on at least a portion of a surface thereof.

37. A method of using an adhesive article, the method comprising:
providing an adhesive article comprising a backing and the pressure sensitive adhesive composition of claim 35 disposed on at least a portion of a surface thereof, and
adhering the adhesive article to skin.

38. A method of making a pressure sensitive adhesive composition, the method comprising combining under conditions effective to cause polymerization:
- at least one monoethylenically unsaturated (meth)acrylic acid ester monomer, which when homopolymerized, has a Tg of less than about 25° C.;
- at least one quaternary ammonium monomer, wherein the quaternary ammonium monomer, when homopolymerized, has a Tg of at least about 25° C.; and
- at least one poly(alkylene oxide) (meth)acrylic acid ester monomer;
- wherein the pressure sensitive adhesive polymer is functionalized with quaternary ammonium functional groups, and further wherein the quaternary ammonium functional groups are covalently bonded to the polymer.

39. The method of claim 38 wherein the monomers are copolymerized prior to the addition of at least one nonreactive poly(alkylene oxide) polymer.

40. The method of claim 38 wherein the monomers are copolymerized prior to the addition of at least one antimicrobial agent.

* * * * *

UNITED STATES PATENT AND TRADEMARK OFFICE
CERTIFICATE OF CORRECTION

PATENT NO.        : 7,005,031 B2
APPLICATION NO.   : 10/052032
DATED             : February 28, 2006
INVENTOR(S)       : Donald H. Lucast It is certified that error appears in the above-identified patent and that said Letters Patent is hereby corrected as shown below:

Title Page
Item [56], References Cited, FOREIGN PATENT DOCUMENTS, after
"JP 2-983449B2 11/1999" insert -- SU 1565855 A 03/1988 --.
Item [56], References Cited, OTHER PUBLICATIONS, after "(Ed.)" insert -- , --.
Item [56], References Cited, OTHER PUBLICATIONS, delete "Publicaiton" and insert
-- Publication --, therefore.
Item [56], References Cited, OTHER PUBLICATIONS, delete "(Ed.)." and insert
-- (Ed.), --, therefore.
Item [56], References Cited, OTHER PUBLICATIONS, delete "Handbbook" and
insert -- Handbook --, therefore.

Column 4
Line 4, delete "monethylenically" and insert -- monoethylenically --, therefore.

Column 5
Line 24, delete "are" and insert -- are/is --, therefore.

Column 8
Line 54, delete "monothenically" and insert -- monoethylenically --, therefore.

Column 11
Line 6-7, delete "tetramethylenc" and insert -- tetramethylene --, therefore.

Column 13
Line 22, delete "(poly(allkylene" and insert -- poly(alkylene --, therefore.

Column 16
Line 58, delete "$5 \times 10^8 CFU/ml.$" and insert -- $5 \times 10^8$ CFU/ml. --, therefore.

UNITED STATES PATENT AND TRADEMARK OFFICE
CERTIFICATE OF CORRECTION

| | |
|---|---|
| PATENT NO. | : 7,005,031 B2 |
| APPLICATION NO. | : 10/052032 |
| DATED | : February 28, 2006 |
| INVENTOR(S) | : Donald H. Lucast |

It is certified that error appears in the above-identified patent and that said Letters Patent is hereby corrected as shown below:

<u>Column 26</u>
Line 66, delete "thereof," and insert -- thereof; --, therefore.

Signed and Sealed this

Thirty-first Day of July, 2007

JON W. DUDAS
*Director of the United States Patent and Trademark Office*